United States Patent [19]

Rainin et al.

[11] 4,085,467

[45] Apr. 25, 1978

[54] INTRAOCULAR LENS

[76] Inventors: Edgar A. Rainin, 5747 Tamarack Way, Concord, Calif. 94521; Emery Major, 17 Skylark Dr., Larkspur, Calif. 94939

[21] Appl. No.: 632,834

[22] Filed: Nov. 17, 1975

[51] Int. Cl.² .......................... A61F 1/16; A61F 1/24
[52] U.S. Cl. ............................................................ 3/13
[58] Field of Search .......................................... 3/13, 1

[56] References Cited

U.S. PATENT DOCUMENTS 3,906,551  9/1975  Otter ......................................... 3/13
3,922,728  12/1975  Krasnov ................................... 3/13

Primary Examiner—Ronald L. Frinks
Attorney, Agent, or Firm—Bielen and Peterson

[57] ABSTRACT

An intraocular lens device for insertion within an eye having a lens portion placed against one side of the iris, means for stabilizing the lens portion extending through the pupil, and anchor means passing through an iris opening.

10 Claims, 10 Drawing Figures

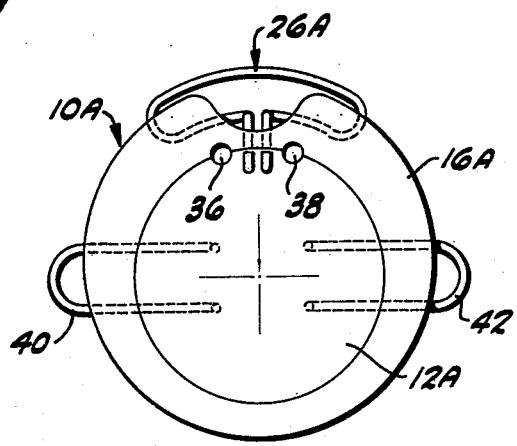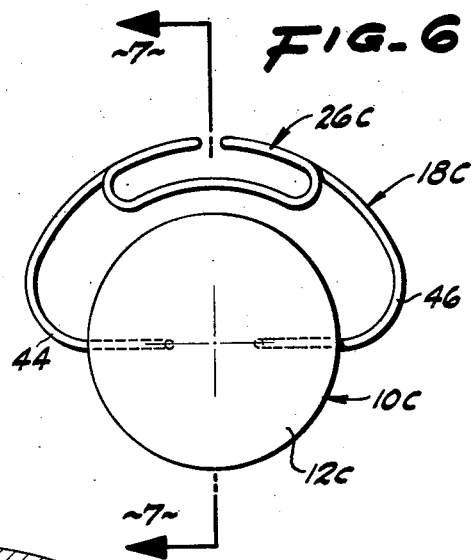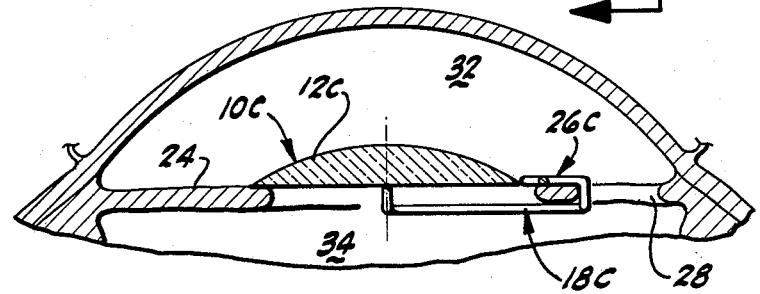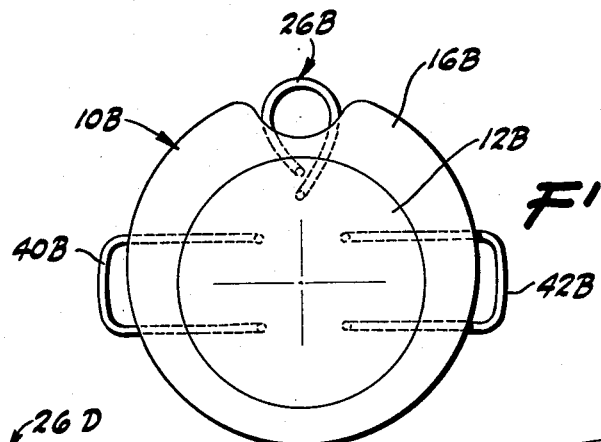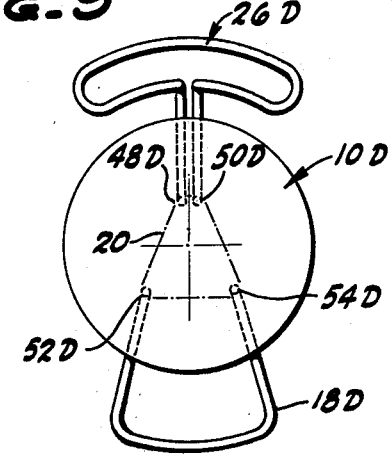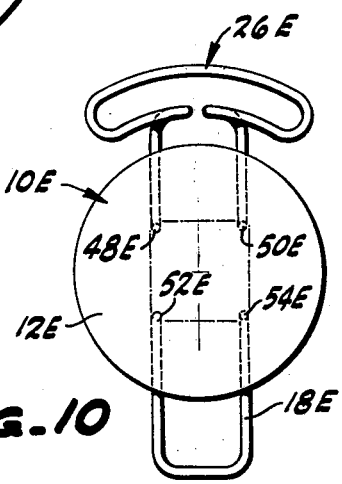

INTRAOCULAR LENS

BACKGROUND OF THE INVENTION

The present invention relates to a novel device usable as an intraocular lens within the eye to correct visual loss which occurs, for example, after cataract removal.

The clouding of the eye's natural lens, located behind the iris, is generally known as a cataract. To prevent blindness the accepted medical procedure entails removal of the natural lens. After removal, the patient's vision must be corrected because of the loss of the lens. Correction of vision has been effected in different ways. The first method fits the patient with spectacles or glasses. However, this reduces peripheral vision by about 65% and magnifies objects seen by about one third. If cataract removal was performed in only one eye, which is often the case, double vision would result because of the magnificaton problem.

Employment of contact lenses represent a better solution, since objects are only magnified by 8–10% and the patient's field of vision remains about the same as before lens removal. However, contact lenses cannot be warn by 50–90% of cataract patients, since they are usually elderly.

The intraocular lens was first conceived by Ridley and implanted in an eye as early as 1949. Dislocation of the lens caused its discontinuance. Later designs included the Lieb lens described un U.S. Pat. No. 2,843,023, which described an auterior chamber lens having loops formed of a thin resilient rod. Corneal dystrophy, and therefore blindness, occured when the loops contact the endothelium on the inner surface of the cornea. The endothelium is a corneal cellular layer which may die upon touching and usually does not regenerate.

Later designs included posterior lenses such as the one described in U.S. Patent to, Flom, No. 3,866,249. Difficulty of insertion of such lenses has precluded their use in most cases.

The most recent anterior chamber designs such as those described in U.S. Pat. No. 3,673,616 to Fedorov et al., and in the Binkhorst-Worst, C. D. "Twenty Years Experience With Pseudophakia: Some Thoughts on the Fixation of Intraocular Lenses", presented at the First International Course of Pseudophekia, Netherlands, June 1974, include loops that pass through the pupils. The most frequent problem encountered is that intraocular lens incorporating later anterior chamber designs tend to dislocate with the opening and closing of the pupil. This has, to a certain extent, been controlled with dilating and constricting chemicals. The Binkhorst-Worst lenses include the design of an anterior hook engaging a posterior loop through an iridectomy opening. Thus, one end of the lens rides with the opening and closing of the sphincter and dilator muscles of the iris. Placement of this lens has proved difficult because the mating of hook and loop is posterior to the iris. Likewise, the Binkhorst-Worst lens having suture holes within the haptic of the lens poses the danger that the suture material will deteriorate with time and will cause a dislocation of the intraocular lens. The use of metal wire sutures has proved undesirable since the maneuvering and fixing of such sutures is difficult.

SUMMARY OF THE INVENTION

In accordance with the present invention of intraocular lens device is provided which overcomes the problems assoicated with the prior art, the lens device includes as its basic elements a lens portion placed against a side portion of the iris covering a portion of the pupil to correct the vision of the eye. The lens has stabilizing means which may take the form of single or multiple loops affixed to the lens portion which extend through the pupil to the other side of the iris with respect to the lens portion. An anchor means passes through an iris opening, such as an iridotomy, and serves to hold the lens over the pupil. The combination of the loop or loops with the anchor means secures the lens to a portion of the iris.

The loop and anchor means may be separate or integral or contiguous. The loop may take variety of forms, such as semicircular, serpentine, winged and the like.

The lens portion may be placed anteriorly or posteriorly in relation to the iris and may include a lens and a haptic affixed thereto. Suture holes may be provided in the lens and haptic to back-up the anchor means to positively prevent dislocation of the lens device while in use.

The anchor means may be effected in a number of ways including a flexible loop of generally oval configuration, a deformable generally T-shaped loop and the like. The anchor means may pass through the iridotomy from either side of the iris.

The device may have many equivalent structures, some of which will be further explained herein.

It is an object of the present invention to provide an intraocular lens to correct the vision of an eye after cataract removal.

It is another object of the present invention to provide a lens device mountable on a side of the iris and fixed thereto correcting the vision of the eye during dilation and constriction of the pupil.

It is yet another object of the present invention to provide a lens device which utilizes an opening in the iris to anchor the lens to the iris.

Another object of the present invention is to provide a device to correct the vision of an eye after extra capsular or intracapsular cataract removal with a minimum possibility of dislocation of the device or interference with the normal functioning of the eye.

Yet another object of the present invention is to provide an intraocular lens device to safely and efficiently correct the vision of the eye better than can be obtained with the use of spectacles or contact lens.

The invention possesses other objects and advantages, especially as concerns particular features and characteristics thereof, which will become apparent as the specification continues.

BRIEF DESCRIPTION OF THE DRAWINGS

FIG. 5 is a plan view of an alternate embodiment of the device.

FIG. 6 is a plan view of an alternate embodiment of the device.

FIG. 7 is a sectional view taken along line 7—7 of FIG. 6.

FIG. 8 is a plan view of an alternate embodiment of the device.

FIG. 9 is a plan view of an alternate embodiment of the device.

FIG. 10 is a plan view of an alternate embodiment of the device.

DESCRIPTION OF THE PREFERRED EMBODIMENTS

Figure 2:
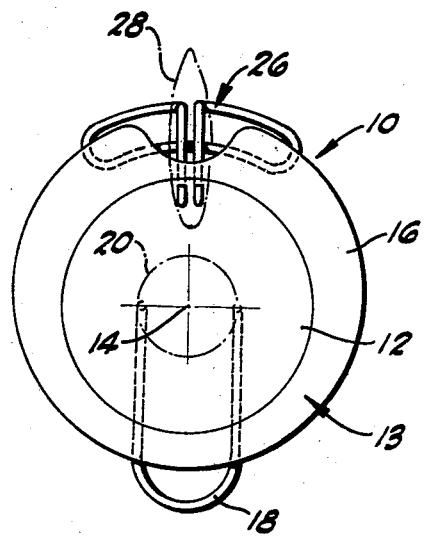
FIG. 2 is a plan view of an embodiment of the device.

The device as a whole is depicted by reference character 10 and alternate embodiments are subsequently identified by the reference character and a letter eg: 10A, 10B, etc. The device 10 (FIG. 2) includes a lens 12 of biconvex or plano-convex configuration having an optical center 14. The lens may be constructed of transparent non-reactive material such as monomer-free polymethylmethacrylate and the like.

Figure 1:
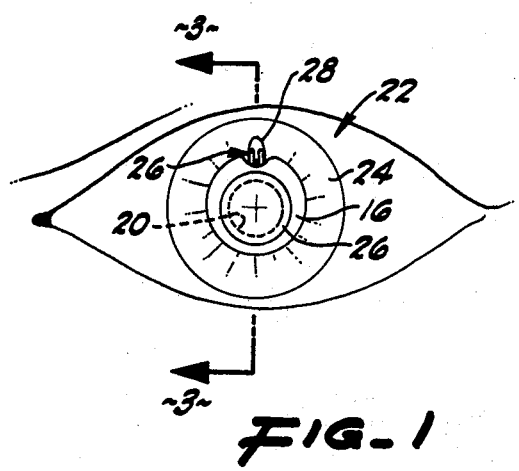
FIG. 1 is a plan view of the device after placement in an eye.
Figure 3:
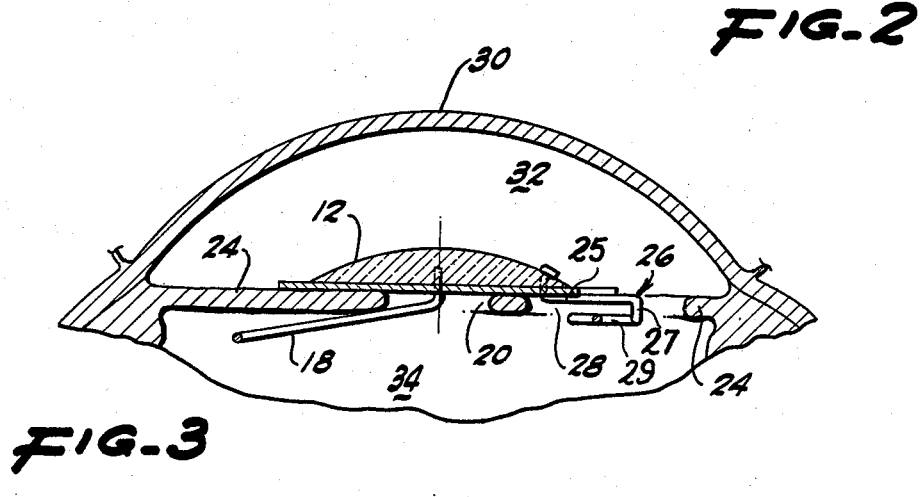
FIG. 3 is a sectional view taken along line 3—3 of FIG. 1

The device 10 may also include a haptic 16 to provide ease in handling the device 10, but imparts no optical function to lens 12. The lens portion 13 includes lens 12 and a haptic 16 in certain cases. The device 10 further shows means for stabilizing the lens portion 13, for example, at least one loop 18 affixed to the lens 12 and extending through the pupil 20 of eye 22, (Pupil shown in phantom in FIGS. 1 and 2) which has an iris 24. Loop 18 may rest against a portion of iris 24, as shown in FIG. 3, but in any case, positions on the opposite side of iris 24 from lens portion 13. The loop 18 may be composed of platinum, platinum alloy, nylon, gold, titanium and the like; the criteria being that the loop material is non-reactive to the body tissue and capable of being fixed to the lens 12. Loop 18 may also be affixed to the haptic 16, if necessary.

The device 10 also includes as one of its elements means 26 for anchoring the lens 12 such that it lies over the pupil 10 and correct the vision of eye 22. The anchoring means 26 may be the structure shown in FIGS. 2-4 where a roughly T-shaped loop is formed, which extends through an iris opening 28. Anchor means 26 in FIGS 1-10 consists of a member having an end 25 connected to lens portion 13, an intermediate portion 27 passing through iris opening 28, and a terminus 29 which is enlarged. Terminus 29 has a dimension wider than the width of iris opening 28. The insertion of anchor means 26 will be more fully explained as the specification continues. As with loop 18, the construction materials are the same when anchor means 26 takes the configuration shown. The anchor means 26 may be flexible, rigid or rigid and deformable depending on the desired structure.

Figure 4:
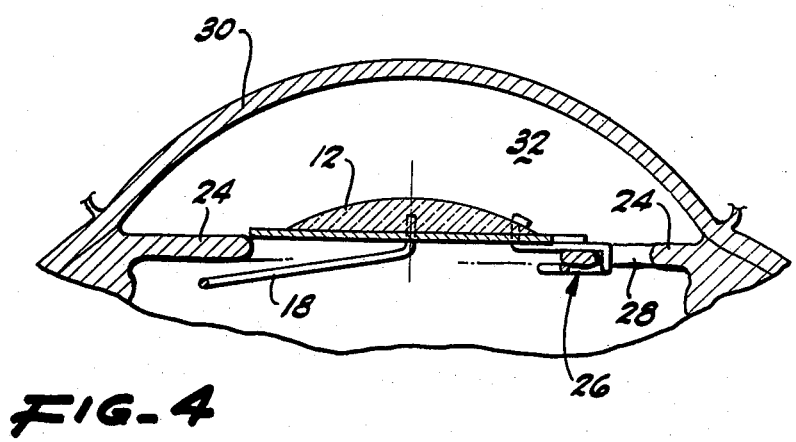
FIG. 4 is a sectional view similar to FIG. 3 but with a dilated pupil.

Turning to FIGS. 3 and 4, the device 10 positions beneath cornea 30 and, in this case, on the outer side of iris 24 or in the anterior chamber 32 of eye 22. The loop 18 passes through pupil 20 into the posterior chamber 34. The natural lens of the eye has been removed ie: intracapsular cataract removal, but the device 10 will perform its task equally whether intracapsular or extracapsular (a bowl-shaped portion of the natural lens remains) cataract removal takes place. As will be observed, the anchor means 26 fits within opening 24, which is preferably an iridotomy as shown in FIGS. 1-4 (to be further explained hereafter). FIG. 3 represents the relatively constricted pupil, about two (2) millimeters in diameter. The device 10 maintains its optical center above a portion of the pupil 20, thus correcting the vision of eye 22. FIG. 4 illustrates a drastic dilation of the eye to 7 or 8 millimeters in diameter, which may naturally occurs in darkness or during excitment. As can be seen, the device 10 resists dislocation since the anchor means 26 rests on the iris 24. It should be noted that the force of gravity acts to pull the device 10 from right to left in FIGS. 3 and 4. As described in FIG. 1, the eye is right side up; anchor means 26 associated with iridotomy 28 in the upper portion of eye 22. As can be seen, the device 10 works well in an opening 28 that has a long vertical dimension, although this is not absolutely necessary to its functioning properly.

As an indication of the relative size of the device 10 and its environment, the lens 12 has a diameter of about 5 millimeters and the lens portion 13 having both a lens 12 and haptic 16, measures about 6 millimeters in diameter (the diameter of a typical human iris is 11 to 12 millimeters). The loops 18 and anchor means 26 of device 10 have a maximum radius of 3.5 to 4.0 millimeters to prevent endothelial touch and minimize inflamation of the surrounding tissue when in place.

Turning to FIG. 5, another embodiment of the device 10A is depicted including a lens 12A, haptic 16A, and anchor means 26A. The device 10A also provides suture holes 36 and 38 to allow the insertion of sutures through the iris as a back-up to anchor means 26A. Loops 40 and 42 prevent dislocation of the device 10A toward the anterior chamber 32 and cornea 30.

FIG. 8 illustrates yet another variation of the device, 10B, which includes loops 40B and 42B which set in the posterior chamber 34 The anchor means 26B represents a flexible loop attached to either the lens 12B or haptic 16B. The loop of anchor means 26B may be constructed of nylon, spring steel or any non-reactive resilient material.

FIG. 6 represents another lens structure 10C which includes a lens 12C without a haptic. The anchor means 26C is integral with loop 18C having wings 44 and 46 that perform the same function as loops 40 and 42 of device 10A. In contast, the anchor means 26C is a termination of the loop 18C and passes through iris opening 28 from the posterior chamber 34 to the anterior chamber 32, as clearly shown in FIG. 7.

Other embodiments of the device 10 include lens devices 10D and 10E in FIGS. 9 and 10. Anchor means 26D and 26E are similar to anchor means 26C in that they pass through opening 28 from the posterior to the anterior chambers 34 and 32. The anchor means 26D includes posts 48D and 50D affixed to lens 10D. In comparison, the device 10E has posts 48E and 50E which are further apart than posts 48D and 50D. Loops 18D and 18E include posts 52D and 52E and 54D and 54E appending from lens 12D and 12E respectively. When pupil 20 (shown in phantom) constricts the posts 48D, 50D, 52D and 54D would form the pupil 20 into a roughly triangular shape while posts 48E, 50E, 52E and 54E would form pupil 20 into a roughly square shape. Either shape has been found to permit excellent vision of eye 22 in combination with device 10D and 10E.

In operation, the lens device 10 is placed against the iris 24 after partial or entire removal of the natural lens of the eye and incision in the cornea. The iris opening 28 is made, which permits use of the anchor means 26. A normal cataract operation requires an iridectomy or iridotomy to permit flow of aqueous humor from the posterior chamber 34 to the anterior chamber 32.

The anchor means 26 is inserted through the iris opening 28 either from the anterior chamber 32 to the posterior chamber 34 or visa versa and the loop or loops 18 are placed on the opposite side of the iris 24 with respect to the lens 12. Where the anchor means 26 is a flexible loop 26B the insertion is performed by squeezing the loop together to form a elongated body that slips through the iris opening. Where the anchor means 26 is a rigid member, the anchor maneuvers into place by stretching the opening 28, similar to the process of opening a button hole before insertion of a button; and then inserting the anchor means 26. Anchor means 26 may also take the form of a deformable body that can be twisted to fit within the opening 28 and then retwisted to prevent its passing back through the opening 28. The anchor means should be fixed to the portion of the iris in the vicinity of the iris opening 28, as an end result. In addition, the anchor may travel along a portion of the iridotomy 28, as heretofore explained during dilation and constriction of the pupil.

While in the foregoing specification, embodiments of the invention have been set forth in considerable detail for purposes of making a complete disclosure of the invention, it will be apparent to those of ordinary skill in the art that numerous changes may be made in such details without departing from the spirit and principle of the invention.

What is claimed is:

1. An intraocular lens device intended for insertion within the eye; the iris of the eye having at least an opening therethrough comprising:
   a. lens portion intended for placement against a side of the iris, said lens portion adapted for covering at least a portion of the pupil;
   b. means for stabilizing said lens portion, said stabilizing means affixed to said lens portion and intended to extend through the pupil of the eye to the side of the iris opposite that of said lens portion placement;
   c. means for anchoring said lens portion intended for extending through the iris opening and affixed to said lens portion such that said lens portion lies over the pupil of the eye, said anchoring means comprising a member connected to said lens portion, said member having an intermediate portion intended for passing through the iris opening, said member having a terminus which is enlarged and has a dimension greater than the width of the iris opening.

2. The lens device of claim 1 in which said lens portion comprises a lens and a haptic affixed to said lens.

3. The device of claim 2 in which said lens portion includes at least one opening therethrough for accepting sutures to fix said lens portion to the iris of the eye.

4. The device of claim 1 in which said stabilizing means includes at least one loop affixed to said lens portion.

5. The device of claim 4 in which said anchor means comprises a loop affixed to said lens portion and having a generally T-shaped portion at is termination.

6. The device of claim 5 in which said anchor means is deformable on the long axis of the T-shaped portion to prevent the cross portion of said T-shaped portion from passing through the the iris opening after said cross portion has passed through the iris opening from one side of the iris to the other side of the iris.

7. The device of claim 4 in which said anchor means comprises a flexible loop adapted to pass through said iris opening when compressed into an elongated body and prevented from passing back through the iris opening when said compression is released.

8. The device of claim 1 in which said stabilizing means and said anchor means comprise a single loop; said loop terminating in said anchor means for passing through the iris opening from the stabilizing means side of the iris to the lens portion side of the iris.

9. The device of claim 8 in which said anchor means is deformable on the long axis of the T-shaped portion to prevent the cross portion of said T-shaped portion from passing through the iris opening after said cross portion has passed through the iris opening from one side of the iris to the other side of the iris.

10. The device of claim 1 in which said anchor means is a loop affixed to said lens portion; said loop adapted to pass through the pupil and the iris opening.

* * * * *